US00PP33857P2

(12) United States Plant Patent
Schoone

(10) Patent No.: US PP33,857 P2
(45) Date of Patent: Jan. 11, 2022

(54) ***PHALAENOPSIS* PLANT NAMED 'PRECIOUS LOVE'**

(50) Latin Name: *Phalaenopsis hybrida*
Varietal Denomination: Precious Love

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 17/339,962

(22) Filed: Jun. 5, 2021

Related U.S. Application Data

(60) Provisional application No. 62/705,003, filed on Jun. 6, 2020.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

UPOV hit on *Phalaenopsis* plant named, 'Precious Love', QZ PBR 2020/2190, filed Sep. 17, 2020.*

* cited by examiner

*Primary Examiner* — Anne Marie Grunberg
(74) *Attorney, Agent, or Firm* — C. Anne Whealy

(57) ABSTRACT

A new and distinct cultivar of *Phalaenopsis* plant named 'Precious Love', characterized by its upright plant habit; moderately vigorous to vigorous growth habit; strong flowering stems; strong leaves; freely flowering habit with typically two inflorescences per plant, each inflorescence with numerous flowers; purplish pink-colored flowers with darker purplish pink-colored stripes and venation; and good postproduction longevity.

2 Drawing Sheets

Figure 1:
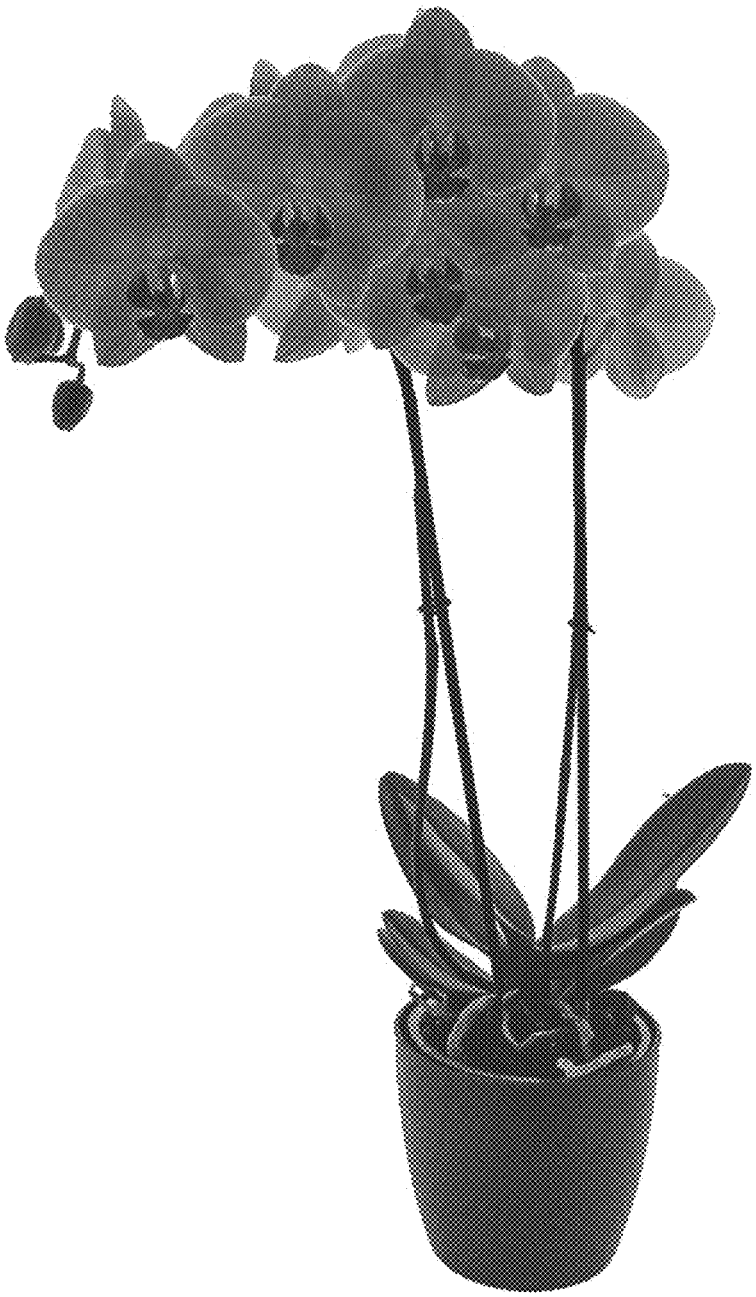

Botanical designation: *Phalaenopsis hybrida.*
Cultivar denomination: 'PRECIOUS LOVE'.

BACKGROUND OF THE INVENTION

The present invention relates to a new and distinct cultivar of *Phalaenopsis* plant, botanically known as *Phalaenopsis hybrida*, and hereinafter referred to by the name 'Precious Love'.

The new *Phalaenopsis* plant is a product of a planned breeding program conducted by the Inventor in Den Hoorn and Heemskerk, The Netherlands. The objective of the breeding program is to develop new fast-growing and freely flowering *Phalaenopsis* plants with good leaf shape and large flowers with unique and attractive patterns and coloration.

The new *Phalaenopsis* plant originated from a cross-pollination in January, 2011 in Den Hoorn, The Netherlands of a proprietary selection of *Phalaenopsis hybrida* identified as code number ST 3970, not patented, as the female, or seed, parent with a proprietary selection of *Phalaenopsis hybrida* identified as code number ST 3676, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in August, 2017.

Asexual reproduction of the new *Phalaenopsis* plant by in vitro meristem propagation in a controlled environment in Assendelft, The Netherlands since August, 2018 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Precious Love'. These characteristics in combination distinguish 'Precious Love' as a new and distinct *Phalaenopsis* plant:

1. Upright plant habit.
2. Moderately vigorous to vigorous growth habit.
3. Strong flowering stems.
4. Strong leaves.
5. Freely flowering habit with typically two inflorescences per plant, each inflorescence with numerous flowers.
6. Purplish pink-colored flowers with darker purplish pink-colored stripes and venation.
7. Good postproduction longevity.

Plants of the new *Phalaenopsis* can be compared to plants of the female parent selection. Plants of the new *Phalaenopsis* differ primarily from plants of the female parent selection in flower color as plants of the new *Phalaenopsis* have purplish pink-colored flowers with darker purplish pink-colored stripes and venation whereas plants of the female parent selection have light purple-colored flowers with little to no distinct venation.

Plants of the new *Phalaenopsis* can be compared to plants of the male parent selection. Plants of the new *Phalaenopsis* differ primarily from plants of the male parent selection in flower color as plants of the new *Phalaenopsis* have purplish pink-colored flowers with darker purplish pink-colored stripes and venation whereas plants of the male parent selection have light violet-colored flowers without stripes and distinct venation.

Plants of the new *Phalaenopsis* can be compared to plants of *Phalaenopsis hybrida* 'Gallery Play', disclosed in U.S. Provisional Patent application Ser. No. 62/705,003 and in a U.S. Plant Patent application filed concurrently having U.S. patent application Ser. No. 17/339,960. In side-by-side comparisons, plants of the new *Phalaenopsis* differ primarily from plants of 'Gallery Play' in flower color as plants of the new *Phalaenopsis* have purplish pink-colored flowers with darker purplish pink-colored stripes and venation whereas plants of 'Precious Love' have pale purple-colored flowers with reddish purple-colored stripes and venation.

Plants of the new *Phalaenopsis* can also be compared to plants of *Phalaenopsis hybrida* 'Good Karma', disclosed in U.S. Provisional Patent application Ser. No. 62/705,003 and in a U.S. Plant Patent application filed concurrently having U.S. patent application Ser. No. 17/339,971. In side-by-side comparisons, plants of the new *Phalaenopsis* differ primarily from plants of 'Good Karma' in flower color as flowers of plants of the new *Phalaenopsis* have less dense venation and stripes than flowers of plants of 'Good Karma'. In addition, the curvature of the labellum is stronger in plants of the new *Phalaenopsis* than plants of 'Good Karma'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Precious Love' grown in a container.

Figure 2:
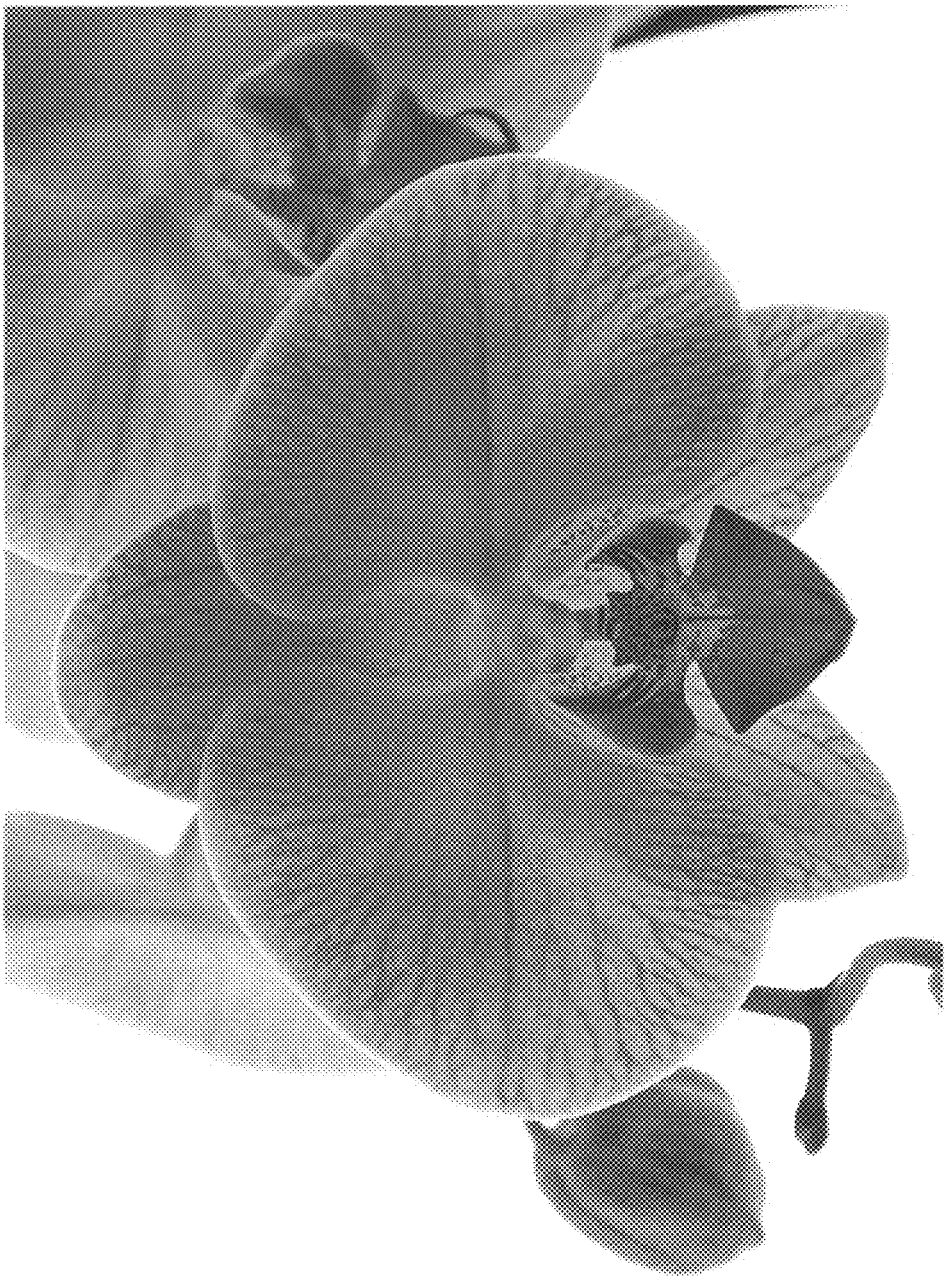

The photograph on the second sheet (FIG. 2) is a close-up view of typical flowers of 'Precious Love'.

DETAILED BOTANICAL DESCRIPTION

The aforementioned photographs and following observations and measurements describe plants grown during the late autumn in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the 18 months of production, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Precious Love'.

Parentage:

*Female parent*.—Proprietary selection of *Phalaenopsis hybrida* identified as code number ST 3970, not patented.

*Male parent*.—Proprietary selection of *Phalaenopsis hybrida* identified as code number ST 3676, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically grey to green in color; actual color of the roots is dependent on substrate composition, water quality, fertilizer, substrate temperature and age of roots.

*Rooting habit*.—Low amount of branching; medium density.

Plant description:

*Plant form and growth habit*.—Herbaceous epiphyte; upright plant habit with typically two inflorescences per plant, each inflorescence with numerous flowers; monopodial; moderately vigorous to vigorous growth habit and moderate growth rate.

*Plant height, substrate level to top of foliar plane*.—About 14 cm.

*Plant height, substrate level to top of inflorescences*.—About 46.2 cm.

*Plant diameter or spread*.—About 29.8 cm.

Leaf description:

*Arrangement and quantity*.—Distichous, simple; sessile; about six leaves per plant.

*Length*.—About 14.6 cm.

*Width*.—About 6.4 cm.

*Aspect*.—Upright to outwardly arching.

*Shape*.—Narrowly obovate; slightly carinate.

*Apex*.—Unequal obtuse.

*Base*.—Sheathing. Sheath length: About 1.4 cm. Sheath width: About 1.4 cm. Sheath color: Close to 144B slightly tinged with close to 146A to 146B.

*Margin*.—Entire; not undulate.

*Texture and luster, upper and lower surfaces*.—Smooth, glabrous; slightly glossy.

*Venation pattern*.—Camptodromous.

*Color*.—Developing leaves, upper surface: Close to NN137A slightly flushed with slightly darker than 191A. Developing leaves, lower surface: Close to 146B; towards the margins, close to NN137B to NN137C. Fully expanded leaves, upper surface: Close to NN137A flushed with slightly darker than 191A; venation, close to NN137A. Fully expanded leaves, lower surface: Close to 146B; towards the margins, close to 146A; venation, close to 137A.

Inflorescence description:

*Appearance and flowering habit*.—Showy zygomorphic flowers arranged on axillary branched racemes; typically two inflorescences per plant; each inflorescence with about ten flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 26.9 cm.

*Inflorescence width*.—About 16.4 cm.

*Flower buds*.—Height: About 2.2 cm. Diameter: About 1.6 cm by 2 cm. Shape: Broadly ovate. Color: Close to 145C; upper surface, distally, tinged with close to N77B.

*Flower size*.—Large, about 8.2 cm (vertical) by 9.1 cm (horizontal).

*Flower depth*.—About 3 cm.

*Petals, quantity and arrangement*.—Three, two lateral petals and one center petal transformed into a labellum.

*Lateral petals*.—Length: About 4.7 cm. Width: About 6.1 cm. Shape: Lunate to reniform; slightly concave. Apex: Shallowly retuse to rounded. Margin: Entire. Texture and luster, upper and lower surfaces: Smooth, glabrous, velvety; matte. Color: When opening, upper surface: Close to N78D; towards the base, close to 76A; venation, close to NN78A and NN78B; finer venation towards the margins and apex. When opening, lower surface: Close to N75D; towards the base, tinged with close to 145C; venation, close to 70B; finer venation towards the margins and apex. Fully opened, upper surface: Close to between N78C and N78D; towards the margins and apex, close to 76D; towards the base, close to 84C to slightly lighter than 84C; venation, close to N78B and NN78B; finer venation towards the margins and apex; color does not change with subsequent development. Fully opened, lower surface: Close to N75C; center and towards the margins, close to 76D; venation, close to 77B; finer venation towards the margins and apex; color does not change with subsequent development.

*Labella*.—Appearance: Three-parted with two lateral lobes and a central lobe. Length, lateral lobes: About 2.3 cm. Width, lateral lobes: About 1.6 cm. Length, central lobe: About 3.7 cm. Width, central lobe: About 6 mm to 22 mm. Shape, lateral lobes: Obovate. Shape, central lobe: Deltoid. Apex, lateral lobes: Obtuse. Apex, central lobe: Cleft with two narrow and strongly recurved cirrose tips, about 1.1 cm in length and about 0.9 mm in width. Margins, lateral lobes: Entire; coarsely undulate. Margins, central lobe: Entire. Texture and luster, upper and lower surfaces: Smooth, glabrous, moderately velvety; matte. Callosities: Located at the base of the labellum and attachment point of the lateral petals; about 5 mm in length, about 7 mm in width and about 5 mm in height. Color: When opening, upper surface: Lateral lobes: Close to N78C; upper margin, close to NN155D; venation, close to NN78A; towards the base, close to 71A slightly tinged with close to 12C and with stripes, close to 156C. Central lobe: Close to NN78C; main vein, darker than NN78A and lateral venation, close to NN78A to NN78B; upper margin strongly tinged with close to 151C; towards the base, close to 157A with radial stripes, close to 185A; cirrose tips, close to NN78A. Callosities: Close to 5D densely covered with fine dots, close to 185A. When opening, lower surface: Lateral lobes: Close to N78C; basal margin tinged with close to 71A; towards the base, close to 156B tinged with close to 157A. Central lobe: Close to 195A; towards the margins and apex, close to NN78A and NN78B; towards the base, close to 84C; at the base, close to 196B; cirrose tips, close to NN78A. Fully opened, upper surface: Lateral lobes: Close to N78C; upper margin, close to NN155D; lower half, close to 71A and with stripes, close to 156C slightly tinged with close to 13B; venation, close to NN78A. Central lobe: Close to NN78B; upper margin, strongly tinged with close to 153A; at the base, close to 157A with radial stripes, close to 185A; main vein, close to N79C; cirrose tips, close to NN78A. Callosities: Close to 6D densely covered with fine dots, close to 185A. Fully opened, lower surface: Lateral lobes: Close to N78D; basal margin tinged with close to 71A and upper margin tinged with close to 22A to 22B; towards the base, close to 156B tinged with close to 157A. Central lobe: Close to 195A; towards the margins, close to 72A; upper margin, close to 60A; towards the base, close to 76C; at the base, close to 196B; cirrose tips, close to NN78A.

*Sepals*.—Quantity and arrangement: Three, one upper dorsal sepal and two lower lateral sepals. Length, dorsal sepal: About 4.6 cm. Width, dorsal sepal: About 3.4 cm. Length, lateral sepals: About 4.7 cm. Width, lateral sepals: About 3 cm. Shape, dorsal sepal: Broadly obovate. Shape, lateral sepals: Ovate. Apex, dorsal sepal: Obtuse to broadly and bluntly acute. Apex, lateral sepals: Acute. Base, dorsal sepal: Truncate. Base, lateral sepals: Cuneate. Margin, dorsal and lateral sepals: Entire. Texture and luster, dorsal and lateral sepals, upper and lower surfaces: Smooth, glabrous, velvety; matte. Color, dorsal sepal: When opening, upper surface: Close to N78C; towards the apex and base, close to 77D; venation, close to N78A; finer venation towards the margins and apex. When opening, lower surface: Close to 182C; towards the base, tinged with close to 147D; venation, close to 183C; finer venation towards the margins and apex. Fully opened, upper surface: Close to between N78C and N78D; towards the margins and apex, close to 76C to 76D; towards the base, close to N75C to N75D; venation, close to between N78A and N78B; finer venation towards the margins and apex; color does not change with subsequent development. Fully opened, lower surface: Close to 77C to 77D; center and towards the base, tinged with close to 147D; venation, close to N78B; finer venation towards the margins and apex; color does not change with subsequent development. Color, lateral sepals: When opening, upper surface: Close to 76D; lower half, close to between 150C and 150D with fine dots, close to 187C; venation, close to N78A; finer venation towards the margins and apex. When opening, lower surface: Close to 145A; venation, close to 183C; finer venation towards the margins and apex. Fully opened, upper surface: Close to 77D; lower half, close to between 146D and 147D with fine dots, close to 187C; venation, close to N78A; finer venation towards the margins and apex. Fully opened, lower surface: Close to 75A; distally tinged with close to 71C; towards the base, close to 145C; venation, close to 72C; finer venation towards the margins and apex.

*Peduncles*.—Length: About 51.9 cm. Diameter: About 5 mm. Strength: Strong. Aspect: Upright to outwardly arching. Texture and luster: Smooth, glabrous; matte. Color: Close to 147A; fine dots, close to 147C to 147D.

*Pedicels*.—Length: About 3.8 cm. Diameter: About 3.25 mm. Strength: Moderately strong. Aspect: About 55° from peduncle axis. Texture and luster: Smooth, glabrous; matte. Color: Close to 147C; proximally, close to 146B to 146C and distally, close to 145C to 145D.

*Reproductive organs*.—Androecium: Column length: About 1 cm. Column width: About 7 mm. Column color: Close to 76C and distally, close to N75B. Pollinia quantity: Two. Pollinia diameter (per two pollinia): About 3 mm. Pollinia color: Close to 23A. Gynoecium: Stigma length: About 4 mm. Stigma width: About 5 mm. Stigma shape: Reniform. Stigma color: Close to N155A. Ovary length: About 8 mm. Ovary diameter: About 1 mm. Ovary color: Close to 145D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate temperatures ranging from about 15° to about 40° C. and are suitable for USDA Hardiness Zones 10 to 12.

It is claimed:

1. A new and distinct *Phalaenopsis* plant named 'Precious Love' as illustrated and described.

* * * * *